(12) United States Patent
Sun

(10) Patent No.: US 6,372,516 B1
(45) Date of Patent: Apr. 16, 2002

(54) LATERAL FLOW TEST DEVICE

(75) Inventor: Ming Sun, Cherry Hill, NJ (US)

(73) Assignee: Sun Biomedical Laboratories, Inc., Blackwood, NJ (US)

( * ) Notice: Subject to any disclaimer, the term of this patent is extended or adjusted under 35 U.S.C. 154(b) by 0 days.

(21) Appl. No.: 09/656,781

(22) Filed: Sep. 7, 2000

(51) Int. Cl.[7] ............................................. G01N 33/53
(52) U.S. Cl. ..................... 436/518; 422/56; 422/58; 422/59; 422/99; 422/60; 422/104; 435/7.1; 435/7.93; 435/7.94; 435/287.7; 435/287.9; 435/288.7; 435/970; 436/514; 436/524; 436/530; 436/541; 436/807
(58) Field of Search .................. 422/56, 58, 99, 422/59, 60, 104; 435/7.1, 7.93, 7.94, 287.7, 287.9, 288.7, 970; 436/518, 524, 530, 541, 807

(56) References Cited

U.S. PATENT DOCUMENTS

| | | |
|---|---|---|
| 4,246,339 A | 1/1981 | Cole et al. |
| 4,366,241 A | 12/1982 | Tom et al. |
| 4,632,901 A | 12/1986 | Valkirs et al. |
| 4,770,853 A | 9/1988 | Bernstein |
| 4,877,586 A | 10/1989 | Devaney, Jr. et al. |
| 5,238,652 A | 8/1993 | Sun et al. |
| 5,656,448 A | 8/1997 | Kang et al. |
| 5,962,336 A | 10/1999 | Sun |
| 6,046,058 A | 4/2000 | Sun |
| 6,140,136 A * | 10/2000 | Lee |

FOREIGN PATENT DOCUMENTS

WO          88/08534 A1 *    3/1988

* cited by examiner

Primary Examiner—Bao-Thuy L. Nguyen
(74) Attorney, Agent, or Firm—Norman E. Lehrer

(57) ABSTRACT

A immunochromatographical test device including a cap, an absorbent pad, a membrane, a test strip, a holder, and a housing is disclosed. The housing contains the membrane and the test strip which contains immunoreagents. Secured to the holder is the absorbent pad which contains the sample to be tested. The cap fits over the holder and the holder fits within the housing. When the absorbent pad contacts the membrane, the membrane indicates that a proper amount of the sample has been collected. When the absorbent pad contacts the test strip, a reaction, if any, can be observed via a window formed within the housing.

6 Claims, 4 Drawing Sheets

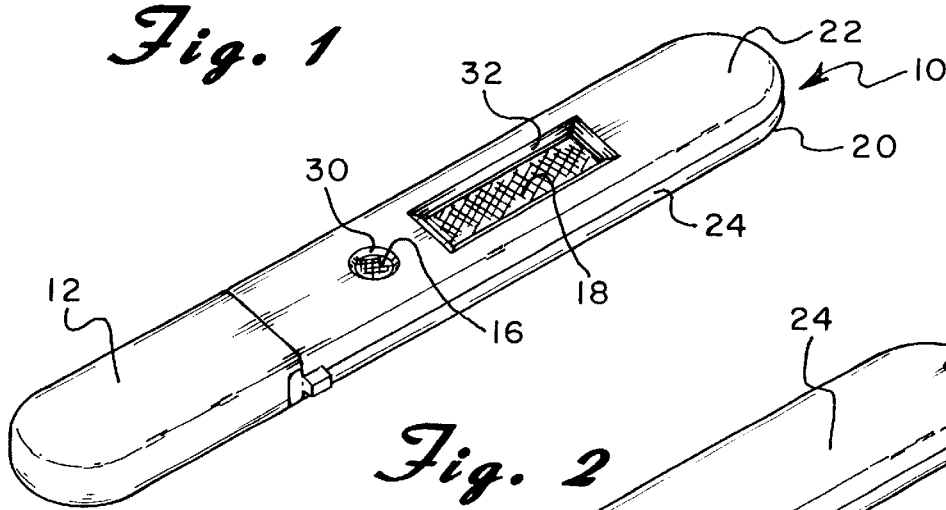
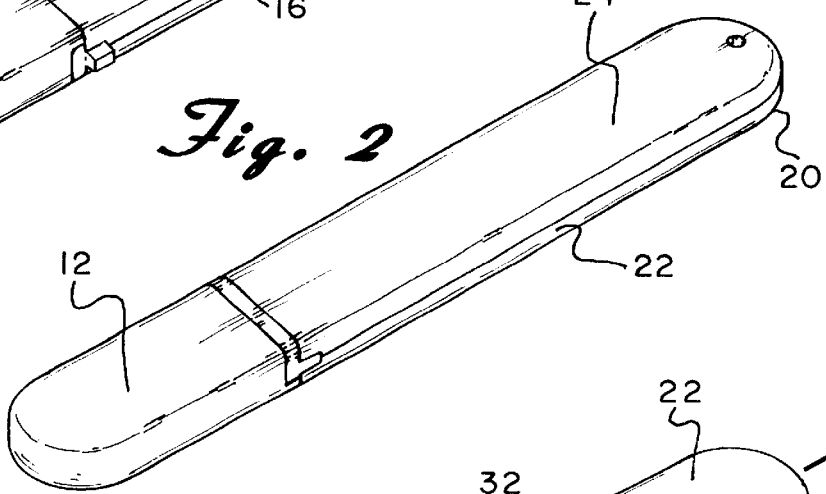
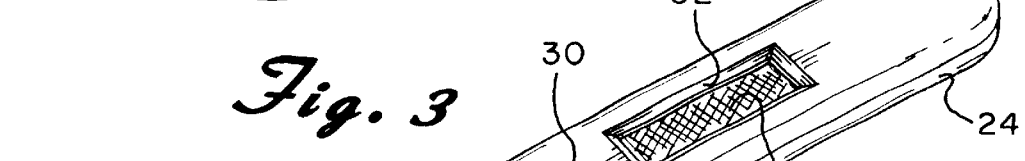
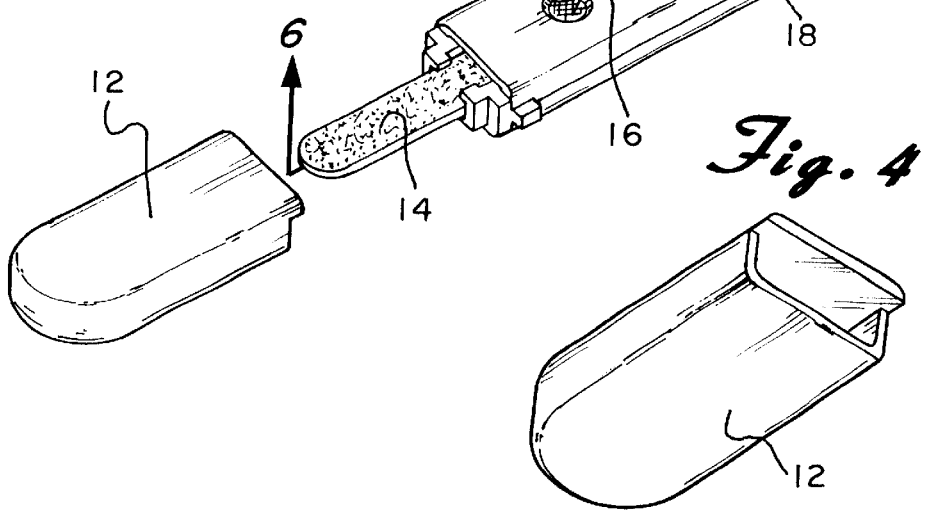

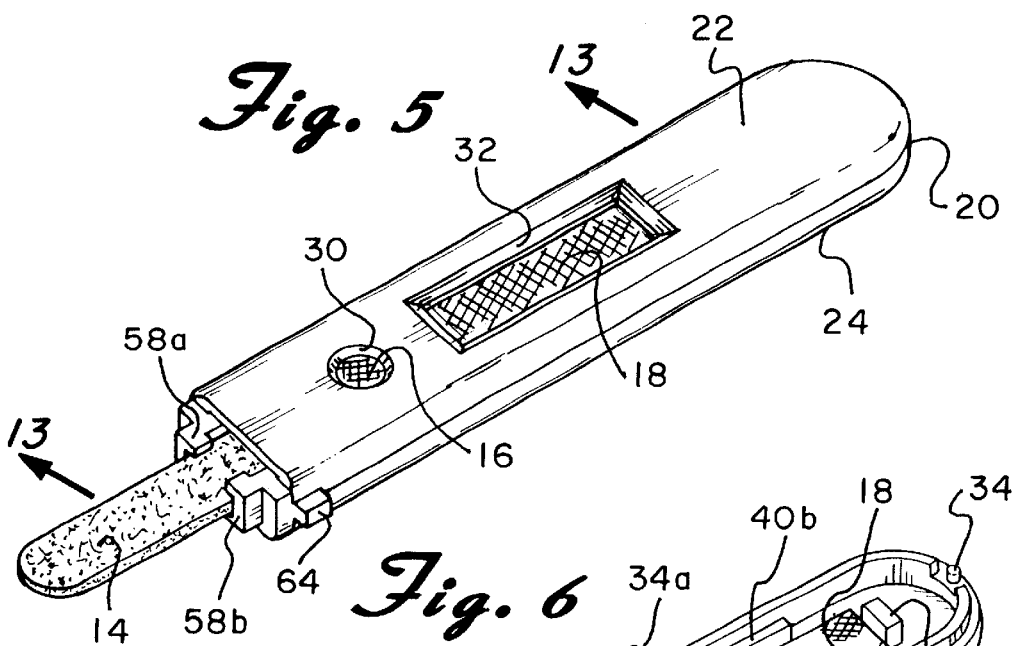
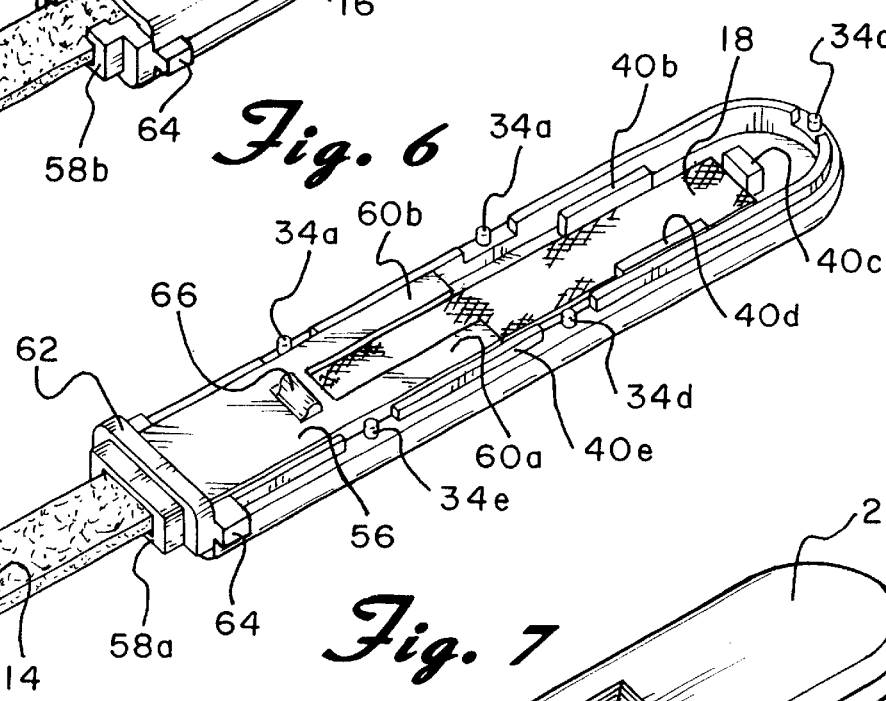
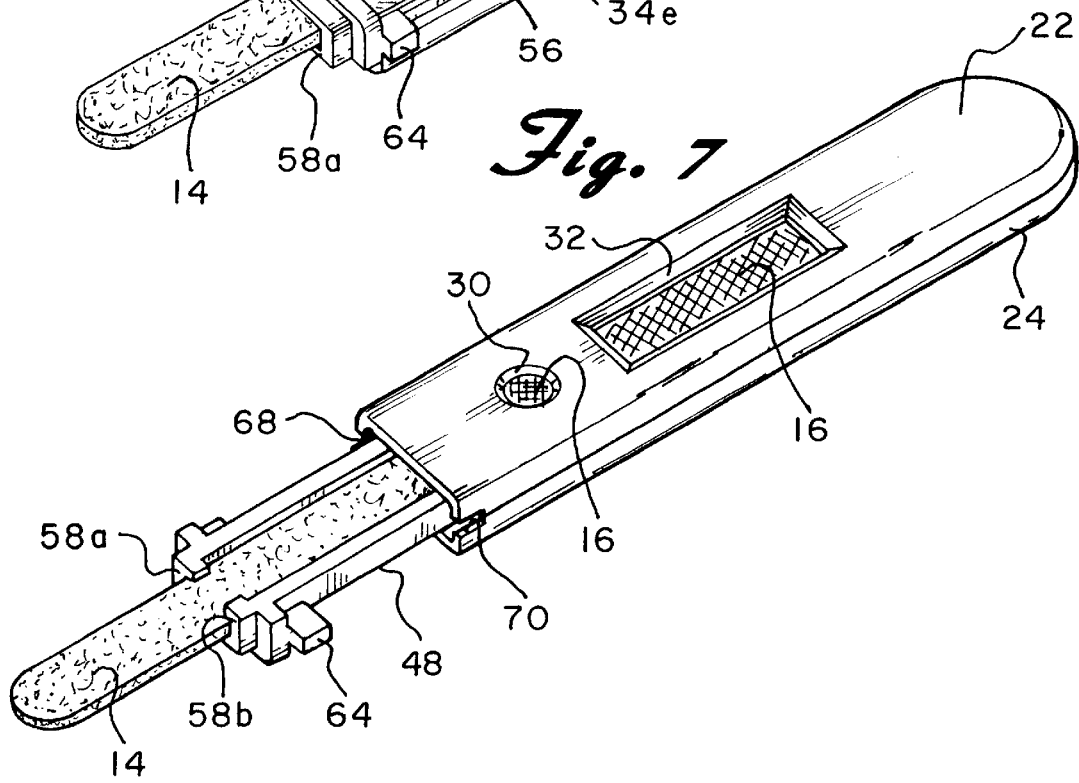

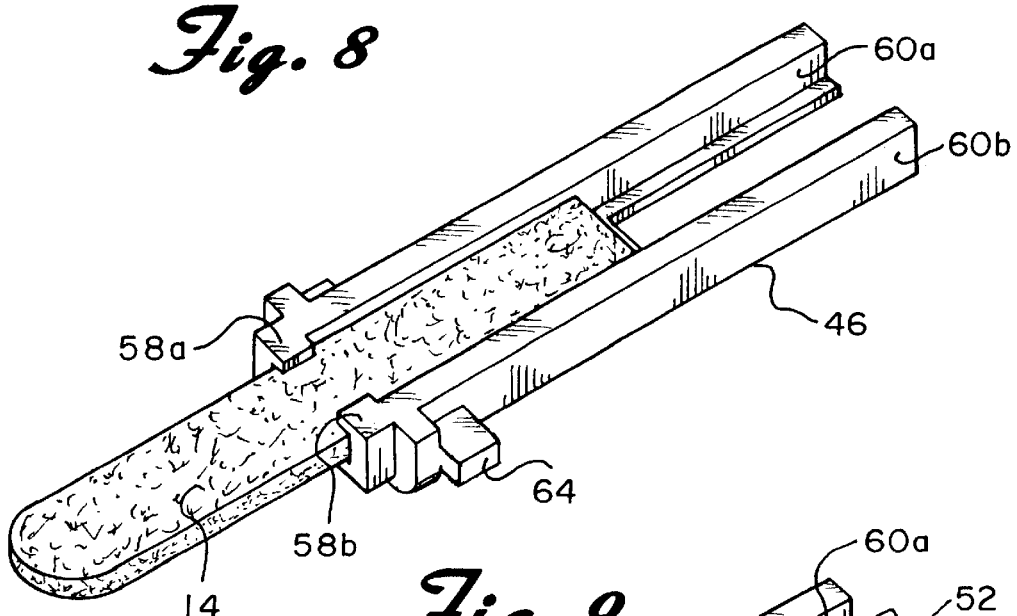
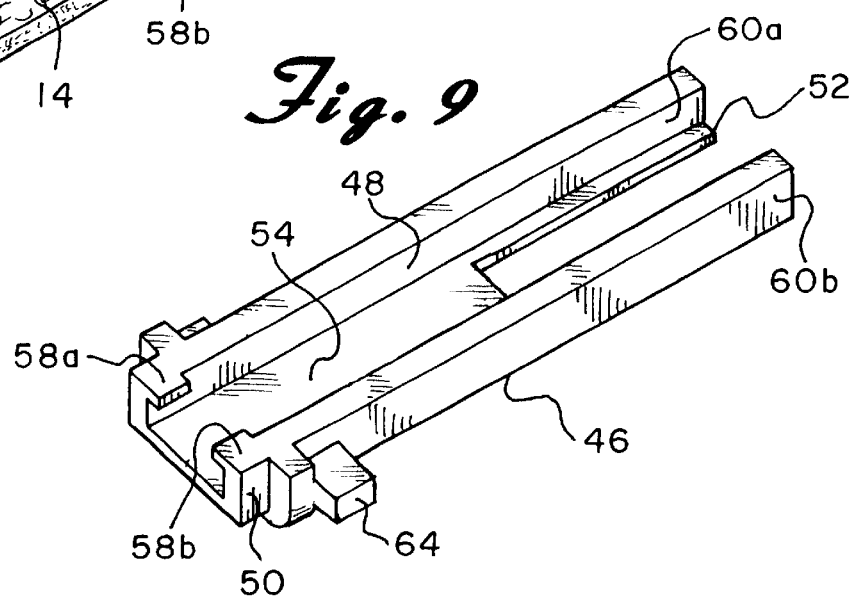
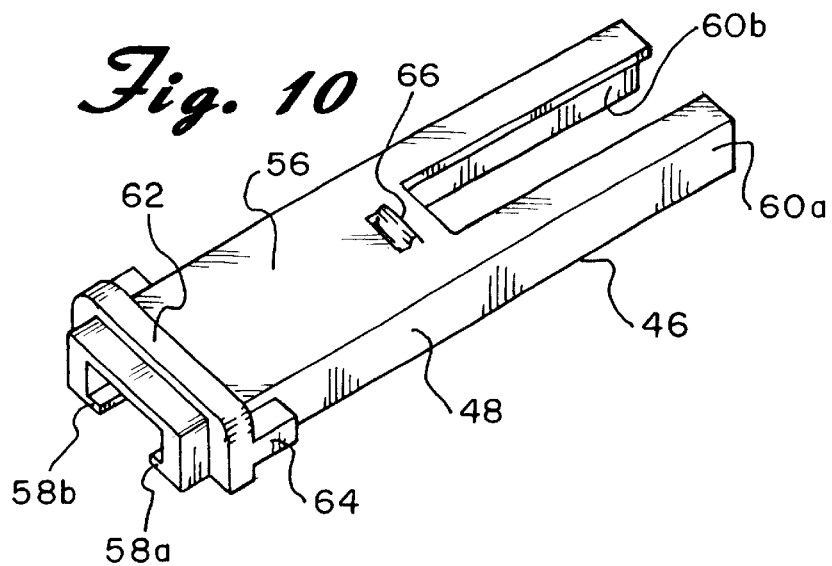

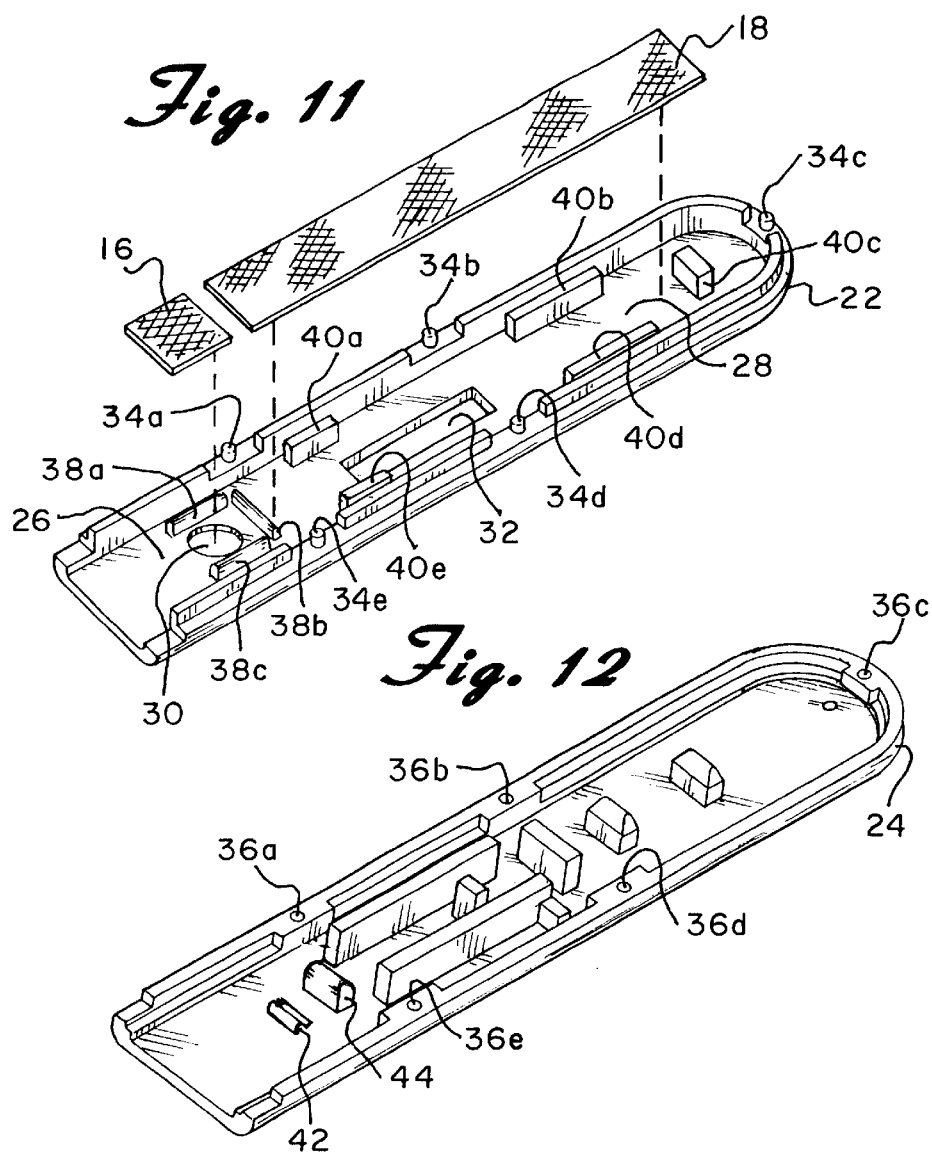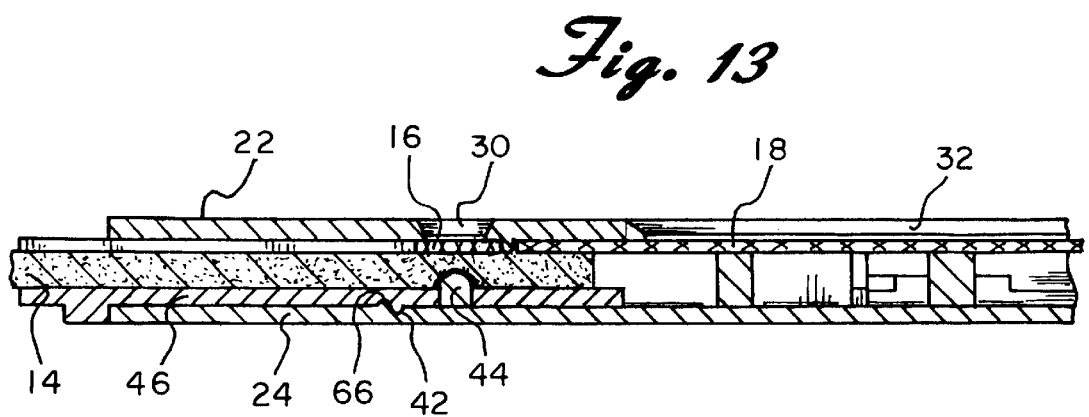

LATERAL FLOW TEST DEVICE

BACKGROUND OF THE INVENTION

The present invention is directed toward a immunochromatographical test device and more particularly, toward a device for detecting the presence of particular substances in a fluid sample.

Various methods for detecting the presence of a particular substance or substances in a fluid sample through the use of immunochemistry are known. Typically, these methods detect both antibodies and antigens and are generally referred to as immunoassays.

For example, U.S. Pat. No. 4,632,901 to Vilkirs discloses an immunoassay device comprising an antibody bound to a porous membrane and to which is added a liquid sample. As the liquid flows through the membrane, target analyte binds to the antibody. Visual detection of labeled antibody indicates the presence of target antigen analyte in the sample. This device, however, requires several steps and a certain amount of expertise by the user in order to avoid inaccurate results.

U.S. Pat. No. 5,656,448 to Kang et al. discloses a dipstick immunoassay device which incorporates the use of symbols in the test zone and enzyme labeled antibodies to detect analytes in a sample of biological fluid. This immunoassay device, however, is complicated to use.

SUMMARY OF THE INVENTION

The present invention is designed to overcome the deficiencies of the prior art discussed above. It is an object of the present invention to provide a test device which determines the presence or absence of certain substances in a test sample.

It is a further object of the present invention to provide a test device which is easy to use and provides accurate results.

In accordance with the illustrative embodiments demonstrating features and advantages of the present invention, there is provided a cap, an absorbent pad, a membrane, a test strip, a holder, and a housing. The housing contains the membrane and the test strip which contains immunoreagents. Secured to the holder is the absorbent pad which contains the sample to be tested. The cap fits over the holder and the holder fits within the housing. When the absorbent pad contacts the membrane, the membrane indicates that a proper amount of the sample has been collected. When the absorbent pad contacts the test strip, a reaction, if any, can be observed via a window formed within the housing.

Other objects, features, and advantages of the invention will be readily apparent from the following detailed description of a preferred embodiment thereof taken in conjunction with the drawings.

BRIEF DESCRIPTION OF THE DRAWINGS

For the purpose of illustrating the invention, there is shown in the accompanying drawings one form which is presently preferred; it being understood that the invention is not intended to be limited to the precise arrangements and instrumentalities shown.

FIG. 1 is a top perspective view of the test device of the present invention;

FIG. 2 is a bottom perspective view of the test device of the present invention;

FIG. 3 is a perspective view of test device and cap of the present invention;

FIG. 4 is a bottom perspective view of the cap of the test device of the present invention;

FIG. 5 is a perspective view of the test device of the present invention;

FIG. 6 is a perspective view similar to FIG. 3 but with the cover removed to reveal the internal parts;

FIG. 7 is a perspective view of the test device of the present invention with the holder extended outwardly;

FIG. 8 is a top perspective view of the carrier of the test device of the present invention with an absorbent pad being held therein;

FIG. 9 is a top perspective view of the carrier of the test device of the present invention without an absorbent pad being held therein;

FIG. 10 is a bottom perspective view of the carrier of the test device of the present invention without an absorbent pad being held therein;

FIG. 11 is an exploded view of the top half of the test device and the membranes of the present invention;

FIG. 12 is a perspective view of the interior of the bottom half of the test device of the present invention; and FIG. 13 is a cross-sectional view taken through line 13—13 of FIG. 5.

DETAILED DESCRIPTION OF THE PREFERRED EMBODIMENT

Referring now to the drawings in detail wherein like reference numerals have been used throughout the various figures to designate like elements, there is shown in FIG. 1 a test device constructed in accordance with the principles of the present invention and designated generally as 10.

The device essentially includes a cap 12, an absorbent pad 14, a membrane 16, a test strip 18, and a housing 20. The housing 20 is an elongated member with a top half 22 and a bottom half 24. The top half 22 has an area 26 therein to receive the membrane 16 and an area 28 to receive the test strip 18. (See FIG. 11.) Both halves 22 and 24 are generally rectangular and may be made from plastic or the like. The top half 22 has a first window 30 through which the membrane 16 may be observed. The top half 22 also has a second, larger window 32 formed therein so that the test strip 18 resting within the housing 20 may be observed therethrough. (See FIG. 1.) The plastic may be clear or opaque. Inside the housing 20, pins 34a–34e are located along the perimeter of the inside surface of the top half 22 with each pin 34a–34e extending into the housing 20. (See FIG. 11.) Each pin 34a–34e fits into a respective hole 36a–36e formed along the perimeter of the inside surface of the bottom half 24 of the housing 20 and holds the two halves 22 and 24 together. (See FIG. 12.)

The membrane 16 is held in place by elongated bumpers 38a–38c located in the interior of the top half 22 of the housing 20. The interior of the top half 22 also has elongated bumpers 40a–40e which aid in holding the test strip 18 in place. (See FIG. 11.) The interior of the bottom half 24 of the housing 20 includes a projection 42 and a stop member 44, the purpose of which will be discussed in greater detail below. (See FIG. 12.)

The membrane 16 contains sensitized dye particles and specific binding reagents or immunoreagents, such as colored latex, colloidal gold conjugate, or other solid phase particles sensitized with immuno-reactive components such as antibodies or antigen derivatives at predetermined sites. Membrane 16 is used to indicate that a sufficient amount of the sample has been collected for the test. This use will be discussed in greater detail below.

The test strip 18 contains an immunochromatographic system which includes a reacting test zone. This test zone contains an immobilized antibody or antigen which is designed to capture the sensitized particles and is used to indicate whether a reaction has taken place. (A more detailed discussion of the immunochromatographic mechanism of the present invention may be found in U.S. Pat. No. 5,238,652 to Sun et al. which is herein incorporated by reference.)

The absorbent pad 14 is secured to a carrier or holder 46. (See FIG. 8.) The absorbent pad 14 may be made from a bibulous, porous material. The holder 46 includes an elongated, generally rectangular body 48 with a first end 50, a second end 52, a top side 54, and a bottom side 56. (See FIGS. 9 and 10.) The body 48 may be made from plastic or the like material. The body 48 of the holder 46 has an area for receiving the absorbent pad 14. The holder 46 also has teeth 58a and 58b which hold the pad 14 in place on the holder 46. Extending from second end 52 are two legs 60a and 60b which fit within the housing 20.

The holder 46 also has a locking member or raised portion 62 extending along the bottom side 56 and the sides of the holder 46. (See FIG. 10.) A thumb or finger grip 64 extends along one side of the locking member 62. (See FIG. 9.) Also located on bottom side 56 of the holder 46 is a protrusion 66.

In order to use the test device, the cap 12 of the test device is removed and the holder 46 with the absorbent pad 14 secured thereto is pulled or pushed outwardly from the device using thumb grip 64 which extends outwardly from the side of the holder. In this position the absorbent pad 14 is not in contact with the membrane 16 and test strip 18. (See FIG. 7.) A sample is obtained from a sample source by dipping the extended portion of the absorbent pad 14 into the source, so that the absorbent pad 14 receives the sample.

The cap 12 is then replaced over the holder 46 and is used to push or otherwise move the holder 46 back into the test device so that the absorbent pad 14 contacts the membrane 16 and the test strip 18. As the holder 46 is pushed into the housing 20, the protrusion 66 contacts and rides over the projection 42 and stop member 44. (See FIG. 13.) The protrusion 66 on the holder 46 is used to further facilitate the absorbent pad 14 to contact the membrane 16. That is, protrusion 66 slides through the housing 20 until it contacts projection 42 and stop member 44. The action of the protrusion 66 contacting the projection 42 forces the absorbent pad 14 upward, thereby forcing the pad 14 to come into contact with the membrane 16. (See FIG. 13.) The holder 46 is prevented from moving farther back into the device by means of the sides of the locking member 62 snapping into place within respective slots 68 and 70 located along the side of the housing 20. Furthermore, this locking mechanism prevents holder 46 from moving independently of the housing 20. (See FIGS. 5 and 7.)

Through first window 30 the user can observe that a proper amount of the sample has been transferred by the membrane 16 being saturated. A dye may be incorporated into the membrane 16. By observation of the removal of this color, the user can be sure that sufficient sample solution is delivered into the device. That is, the disappearance of color indicator signals that a sufficient amount of sample has been collected on the absorbent pad 14.

The sample, via capillary action, migrates to the test strip 18. The absorbent pad 14 and the test strip 18 overlap so that approximately 5–8 millimeters of the absorbent pad 14 contacts the test strip 18. The reaction which occurs may then be observed through the second window 32 on the housing 20. That is, if the sample to be tested contains the antigen which conjugates with the antibody contained in the test strip 18, dye particles contained in the test strip 18 serve as a visual indicator of the specific antigen/antibody reaction.

In another embodiment, the holder 46 with the absorbent pad 14 secured thereon need not be extended outwardly from the test device. That is, in the position illustrated in FIG. 1, the absorbent pad 14 could already be in contact with the membrane 16 and the test strip 18. As seen in FIG. 3, the cap 12 may be removed and the absorbent pad 14 may be contacted with a sample source without extending the holder 46 outwardly as discussed above. Again, as discussed above, the membrane 16 indicates when a sufficient amount of sample has been collected which can be observed through window 30. The absorbent pad 14 is in contact with the test strip 18 so that any reaction that occurs may be observed through window 32.

It should be realized that the membrane 16 itself may include reagents so as to be used for a test, such as an alcohol test. Other supplements may be added to the membrane 16 through first window 30, if other tests are desired.

The present invention provides several advantages over the prior art. For example, the device may be used for sample extraction. That is, the sample may be obtained without centrifugation or column separation. Also, the holder has means for indicating when a sufficient amount of the sample has been extracted from the sample source so that the device works efficiently. Furthermore, the sample collection and reaction initiation are separate so that there is better control of the reaction. Also, the cap may be used for additional pre-incubation or extraction when the device is placed in an up-standing position, with the cap serving as a reacting test tube.

The present invention may be embodied in other specific forms without departing from the spirit or essential attributes thereof and accordingly, reference should be made to the appended claims rather than to the foregoing specification as indicating the scope of the invention.

I claim:

1. A test device comprising:

a housing;

a test strip contained within said housing, said test strip having immunoreagents therein;

a membrane contained within said housing for indicating the saturation of a sample to be tested;

means for retaining said test strip within said housing;

means for retaining said membrane within said housing;

a holder secured to said housing for containing the sample to be tested, said holder having an absorbent material for holding the sample wherein said absorbent material and said holder extend outwardly from said housing; and a cap releasably attached to said holder wherein said cap moves said holder within said housing so that said absorbent material is contacted with said membrane and said test strip after the sample has been collected.

2. The test device of claim 1 further including means for facilitating said absorbent material to contact said membrane.

3. The test device of claim 1 wherein said housing includes a top half and a bottom half.

4. The test device of claim 3 wherein said top half of said housing include said means for retaining said test strip and said means for retaining said membrane therein.

5. The test device of claim 1 further including means for locking said holder to said housing after the sample has been collected.

6. The test device of claim 5 wherein said locking means includes a locking member and said housing includes a slot through which said locking member extends.

* * * * *